United States Patent [19]

Nakamura et al.

[11] Patent Number: 4,657,641
[45] Date of Patent: Apr. 14, 1987

[54] DETERMINATION OF SILICON IN MOLTEN METAL

[75] Inventors: Hajime Nakamura, Hiroshima; Masanori Iwase; Eiji Ichise, both of Kyoto; Takaharu Moriya, Hiroshima; Shigeaki Maruhashi, Tokyo, all of Japan

[73] Assignee: Nisshin Steel Co., Ltd., Tokyo, Japan

[21] Appl. No.: 858,175

[22] Filed: May 1, 1986

[30] Foreign Application Priority Data

May 15, 1985 [JP] Japan ............................... 60-101373

[51] Int. Cl.⁴ ............................................. G01N 27/58
[52] U.S. Cl. ....................................... 204/1 T; 204/422
[58] Field of Search ................ 204/422, 423, 1 T, 1 S, 204/429

[56] References Cited

U.S. PATENT DOCUMENTS 3,403,090 9/1968 Tajiri et al. ..................... 204/1 T X
3,978,006 8/1976 Topp et al. ....................... 204/429 X
4,121,988 10/1978 Sano et al. ........................ 204/429
4,225,634 9/1980 Tanaka et al. ................... 204/429 X
4,233,142 11/1980 Rohr et al. ......................... 204/429
4,342,633 8/1982 Cure ................................... 204/423

FOREIGN PATENT DOCUMENTS 2625873 12/1976 Fed. Rep. of Germany ...... 204/429
67454 4/1984 Japan .................................... 204/429

Primary Examiner—G. L. Kaplan
Attorney, Agent, or Firm—Wenderoth, Lind & Ponack

[57] ABSTRACT

Use of a sensor in the electro-chemical determination of silicon dissolved in a molten metal, said sensor comprising a layer of a solid electrolyte capable of conducting oxygen ions, a reference electrode in contact with one surface of said layer of the solid electrolyte for providing a constant oxygen potential at a particular temperature of measurement, and an auxiliary electrode comprising $SiO_2$ disposed in the immediate vicinity of the other surface of said layer of the solid electrolyte.

3 Claims, 24 Drawing Figures

FIG. 19
FIG. 20
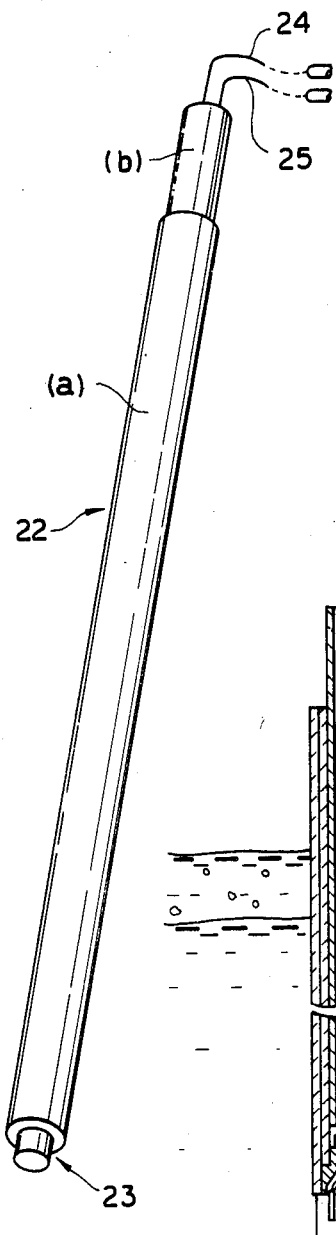
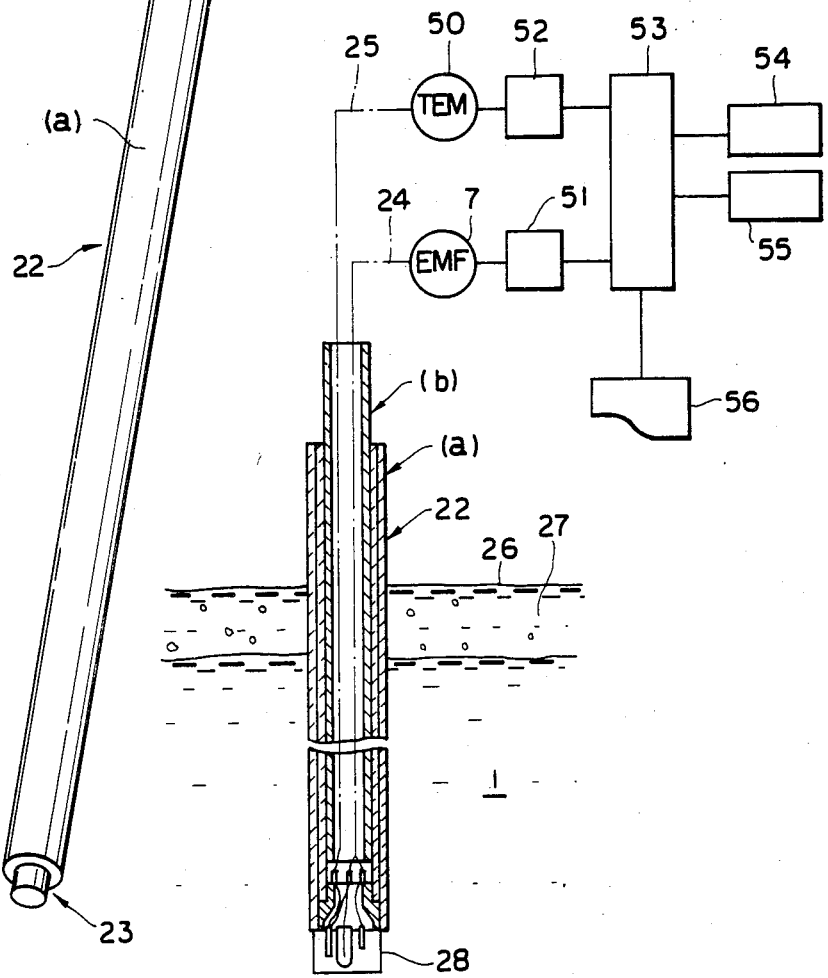

DETERMINATION OF SILICON IN MOLTEN METAL

FIELD OF THE INVENTION

The present invention relates to the electro-chemical determination of silicon dissolved in a molten metal. The invention envisages the use of a certain sensor in the real time determination of the silicon content of a molten metal, and provides a method and apparatus for the electro-chemical determination of silicon dissolved in a molten metal.

PRIOR ART

During the melt refining of metals, for example, in processes for making pig iron or steel, it is frequently required to quickly determine the silicon content of the molten metal being refined. For example, a preliminary treatment of a molten pig iron is widely practiced prior to the treatment of the molten pig iron in a converter. In such a preliminary treatment of the molten pig iron, amounts of treating materials to be added to the molten pig iron must be selected in accordance with the silicon content of the molten pig iron, since the reactions involved in the preliminary treatment greatly depend upon the silicon content of the molten pig iron to be treated. Thus, it is essentially required to quickly determine the silicon content of the molten pig iron during the pretreatment. For the determination of silicon use has heretofore been made of instrumental analyses, including, for example, a so-called quantoback method, which takes a greatly reduced time for analysis when compared with the old chemical analysis.

PROBLEMS THE INVENTION AIMS TO SOLVE

Even with the instrumental analysis, which requires the steps of sampling of the molten pig iron, solidification of the sample, polishing and washing to provide the sample with a surface to be analyzed, about five minutes are taken before the result of the analysis is obtained. This means that if the preliminary treatment is not stopped during the analysis, the result of the analysis can only be obtained when most of the time necessary for the pretreatment of the molten pig iron has elapsed, rendering it difficult to feed back the result of the analysis to take any necessary actions. This has been a cause of undesired variations in the compoment concentrations of the molten pig iron obtained by the preliminary treatment. On the other hand, if the preliminary treatment is stopped during the analysis, the process suffers from the problem of delay in time.

The problems discussed above are not limited to a process for making a pig iron. Likewise in processes for making steels and in processes for refining of molten non-ferrous metals, if the silicon content of the molten metal being processed is determined by instrumental or chemical analyses requiring sampling of the molten metal, the problems discussed above on the troublesome and time-consuming nature of the method of determination are encountered.

The invention aims to solve the problems discussed above, and provides a method and apparatus for the instantaneous determination of the silicon content of a molten metal, based on a principle of a certain concentration cell.

MEASURES TO SOLVE THE PROBLEMS

According to the invention there is provided a method for the electro-chemical determination of silicon dissolved in a molten metal, comprising the steps of placing a solid auxiliary electrode comprising $SiO_2$ in the molten metal to form a chemical quasi-equilibrium zone wherein the activity of $SiO_2$ is substantially constant, and measuring a potental difference between the molten metal and a reference electrode for providing a constant oxygen potential at a particular temperature of measurement separated from each other by a solid electrolyte capable of conducting oxygen ions.

The invention envisages the use of a sensor in the electrochemical determination of silicon dissolved in a molten metal, said sensor comprising:

a layer of a solid electrolyte capable of conducting oxygen ions, a reference electrodce in contact with one surface of said layer of the solid electrolyte for providing a constant oxygen potential at a particular temperature of measurement, and a solid auxiliary electrode comprising $SiO_2$ disposed in the immediate vicinity of the other surface of said layer of the solid electrolyte.

A preferred sensor comprises a tube with one end closed made of a solid electrolyte capable of conducting oxygen ions, a reference electrode sealed in said tube for providing a constant oxygen potential at a particular temperature of measuring, and a solid auxiliary electrode comprising $SiO_2$ disposed in the immediate vicinity of the outer surface of said tube.

Thus, the invention provides a method for the electrochemical determination of silicon dissolved in a molten metal, by means of a device comprising a layer of a solid electrolyte capable of conducting oxygen ions, a reference electrode in contact with one surface of said layer of the solid electrolyte for providing a constant oxygen potential at a particular temperature of measurement, and a means for determining a potential difference between said reference electrode and the molten metal, characterized by placing a solid auxiliary electrode having a constant activity of $SiO_2$ in the molten metal, thereby forming a chemical quasi-equilibrium zone in the vicinity of said auxiliary electrode, the product $[a_{si}] \times [P_{o2}]$, wherein $[a_{si}]$ represents an activity of silicon in the molten metal and $[P_{o2}]$ represents a partial pressure of oxygen in the molten metal, being substantially constant within said chemical quasi-equlibrium zone, bringing the other surface of said layer of the solid electrolyte in contact with said chemical quasi-equilibrium zone, and, measuring a potential difference between the molten metal and said reference electrode.

Whatever molten metals are concerned, the method according to the invention is applicable to the determination of silicon dissolved in the molten metal. However, when applied to the determination of the silicon content of a molten pig iron or steel, the method according to the invention is most attractive, partly because no method that can instantaneously determine the silicon content of a molten pig iron or steel has heretofore been known, and partly because quick determination of silicon is highly needed when processing a molten pig iron or steel. While the invention will now be described with respect to an embodiment in which the molten metal is molten pig iron, it should be appreciated that the description is applicable to cases where non-ferrous molten metals are concerned.

When a concentration or activity of silicon of a molten pig iron is to be determined by means of a concentration cell, it is most likely considered that an electrolyte capable of conducting silicon ions will be needed. The electrolyte should preferably be solid at a temperature of the molten pig iron. However, such an electrolyte which is capable of conducting silicon ions and is solid at a temperature of the measurement is not known, and is not expected to be developed in the near future. Under the circumstances, we looked for a possibility of the transformation of an activity of silicon in a molten pig iron to an oxygen potential. If it is possible to transform the silicon activity to the oxygen potential, it will be sufficient for us to determine the oxygen potential by means of a conventional oxygen concentration cell.

When the solid material having a constant activity of $SiO_2$, that is a solid material comprising $SiO_2$, which is stable in the molten pig iron is placed in a molten pig iron, a chemical equilibrium represented by the equation:

$$Si + O_2 = SiO_2 \text{ ( solid )}$$

will be formed in the immediate vicinity of said material. A zone wherein such a chemical equilibrium prevails will be referred to herein as "a chemical quasi-equilibrium zone". A material having a constant activity of $SiO_2$ which may form the chemical quasi-equilibrium zone when immersed in a molten pig iron will be referred to herein as "an auxiliary electrode". If the auxiliary electrode consists of pure silica, the activity of $SiO_2$ is 1. Whereas if the auxiliary electrode comprises silica and other component or components, the activity of $SiO_2$ is less than 1. In the case wherein the activity of $SiO_2$ is 1. the equilibrium constant K of the above-mentioned chemical equilibrium can be expressed by the following equation:

$$\log K = -\log a\ _{si} - \log P\ _{o_2}$$

wherein $a\ _{si}$ represents an activity of silicon in the molten pig iron and $P\ O_2$ represents a partial pressure of oxygen in the molten pig iron. Whereas, in the case wherein the activity of $SiO_2$ is a constant less than 1, the equilibrium constant K' of the above-mentioned chemical equilibrium can be exressed by the following equation:

$$\log K' = -\log a\ _{si} - \log P\ _{o_2} + (\text{ a constant })$$

The K or K' is a function solely depending upon the temperature, and, thus, is a constant at a particular temperature concerned. Accordingly, if the $P\ O_2$ in a zone wherein the above-mentioned chemical equilibrium prevails (that is the chemical quasi-equilibrium zone) is measured using an oxygen sensor, the $a\ _{si}$ in the same zone can be determined.

Thinking in this way, we have measured the oxygen potential in the chemical quasi-equilibrium zone by means of an oxygen sensor, and interestingly found that the observed electro-motive force fairly corresponds to the silicon content of the molten pig iron. The invention is based on this finding. In our measurement we have used a two phase mixure of $ZrO_2$ and $ZrSiO_4$ as a solid material having a constant activity of $SiO_2$ to form the chemical quasi-equilibrium zone and a stabilized $ZrO_2$ as the solid electrolyte of the oxygen sensor.

With a molten pig iron containing silicon, the oxygen content is extremely low when compared with the silicon content. For example, with a molten pig iron containing from 0.1 to 0.7% by weight of silicon, the oxygen content normally ranges from several to several tens ppm by weight. Accordingly, in the chemical quasi-equilibrium zone formed in such a molten pig iron, the oxygen potential appreciably varies in accordance with a slight change of the oxygen content, in contrast to the silicon content which may only appreciably vary when the silicon content changes to a considerable extent. In other words, in the chemical quasi-equilibrium zone, a change of the silicon content if any is relatively very small, whereas the oxygen potential may measurably vary in response to the oxygen content. By forming the above-mentioned chemical quasi-equilibrium zone in accordance with the invention, it has become possible to make the measurable oxygen potential in the zone to correspond to the silicon content in the zone and in turn to the silicon content of the molten pig iron, the latter being substantially the same as the former.

In the practice of the invention it is essential to form a chemical quasi-equilibrium zone in the molten pig iron, in which zone the activity of $SiO_2$ is constant and the chemical equilibrium represented by the equation:

$$\log K = -\log a\ _{si} - \log P\ _{o_2}$$

or $$\log K' = -\log a\ _{si} - \log P\ _{o_2} + (\text{ a constant })$$

prevails. In other words, It is essential to form a chemical quasi-equilibrium zone in the molten pig iron, in which zone the product $[a\ _{si}] \times [P\ O_2]$ being substantially constant. We utilize an auxiliary electrode to form in the molten pig iron such a chemical quasi-equilibrium zone.

As the auxiliary electrode use can be made of any solid material comprising silica which is stable in a molten pig iron, and thus, which when placed in a molten pig iron, may locally form in the immediate vicinity of said material an equilibrium represented by the equation:

$$Si + O_2 = SiO_2 \text{ ( solid )}.$$

The auxiliary electrode may consist essentially of pure silica. But pure silica is not fully satisfactory, since it tends to be softened in the molten pig iron so that its surface configuration may be deformed owing to flows of the molten pig iron. As the auxiliary electrode we prefer to use compounds, solutions or mixtures of $SiO_2$ with metallic oxides, which are more stable than $SiO_2$ in the molten pig iron, including, for example, oxides of metals of Groups IIA (alkaline earth), I A (alkali), IIIB and IVB of the Periodic Table. In the case wherein the solid electrolyte of the used oxygen sensor consists essentially of at least partly stabilized $ZrO_2$, and the auxiliary electrode is to be supported on the surface of the solid electrolyte, we have found that the use of the auxiliary electrode consisting essentially of a two phase mixture of $ZrO_2$ and $ZrSiO_4$ is particularly preferred in view of its stability and adhesiveness of the solid electrolyte.

An apparatus for the electro-chemical determination of silicon dissolved in a molten metal according to the invention comprises:

a layer of a solid electrolyte capable of conducting oxygen ions, a reference electrode in contact with one surface of said layer of the solid electrolyte for providing a constant oxygen potential at a particular temperature of measurement, a means for determining a potential difference between said reference electrode and the molten metal, and at least one solid auxiliary electrode comprising $SiO_2$ disposed in the immediate vicinity of the other surface of said layer of the solid electrolyte.

By the term "immediate vicinity" we mean that the auxiliary electrode is disposed at such a location relative to the layer of the solid electrolyte that when the silicon sensor is immersed in the molten pig iron the above-mentioned other surface of the layer of the solid electrolyte comes in contact with the chemical quasi-equilibrium zone formed by the auxiliary electrode. For this purpose, the auxiliary electrode may be disposed in contact with or at a location slightly spaced apart from the above-mentioned other surface of the layer of the solid electrolyte.

As the solid electrolyte, reference electrode and means for determining a potential difference between the reference electrode and the molten metal, use can be made of those which have heretofore been used in the electro-chemical determination of oxygen in a molten metal with conventional oxygen sensors.

The method, apparatus and silicon sensor in accordance with the invention will now be further described with reference to the attached drawings, in which:

FIG. 19 is a perspective view of a preferred measuring element in which a silicon sensor according to the invention is incorporated:

FIG. 20 shows a schematic vertical cross-section of the element of FIG. 19 during measurement, and also shows an arrangement of measuring instruments in a block diagram;

Figure 1:
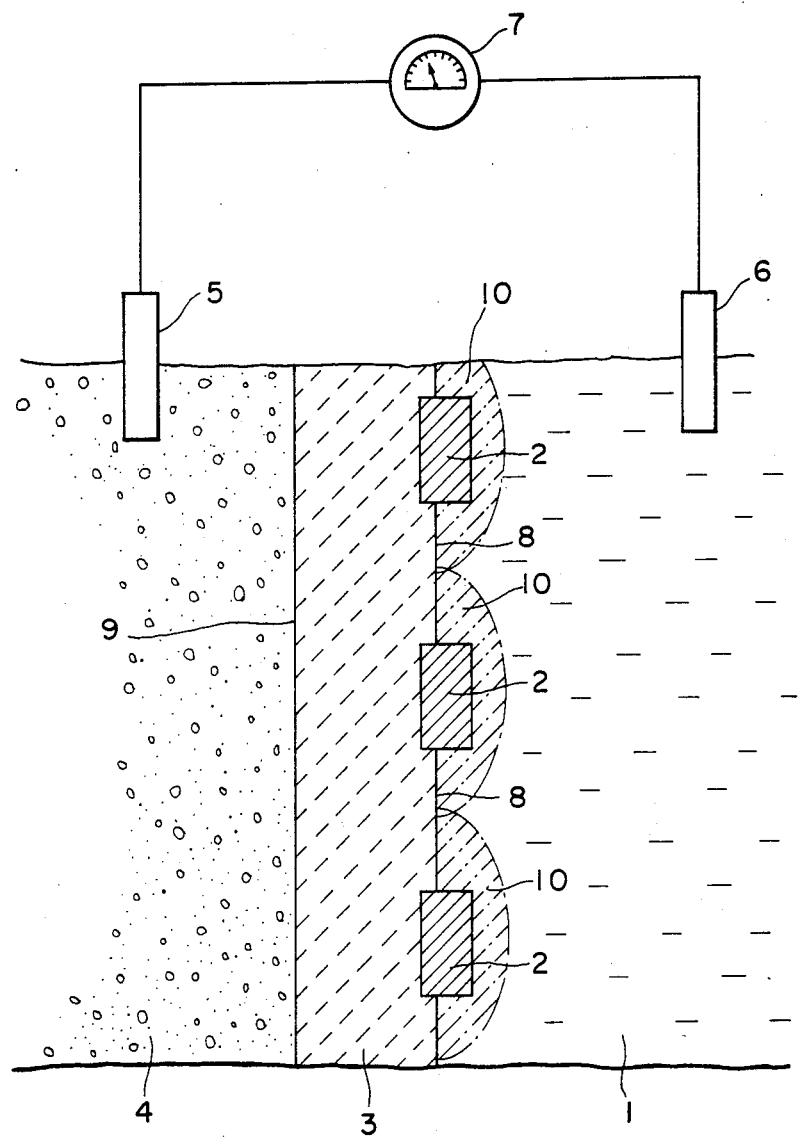
FIG. 1 is a conceptual view for illustrating a principle underlying the determination of the silicon concentration in accordance with the invention, in which the auxiliary electrode is supported on a surface of the solid electrolyte layer.
Figure 2:
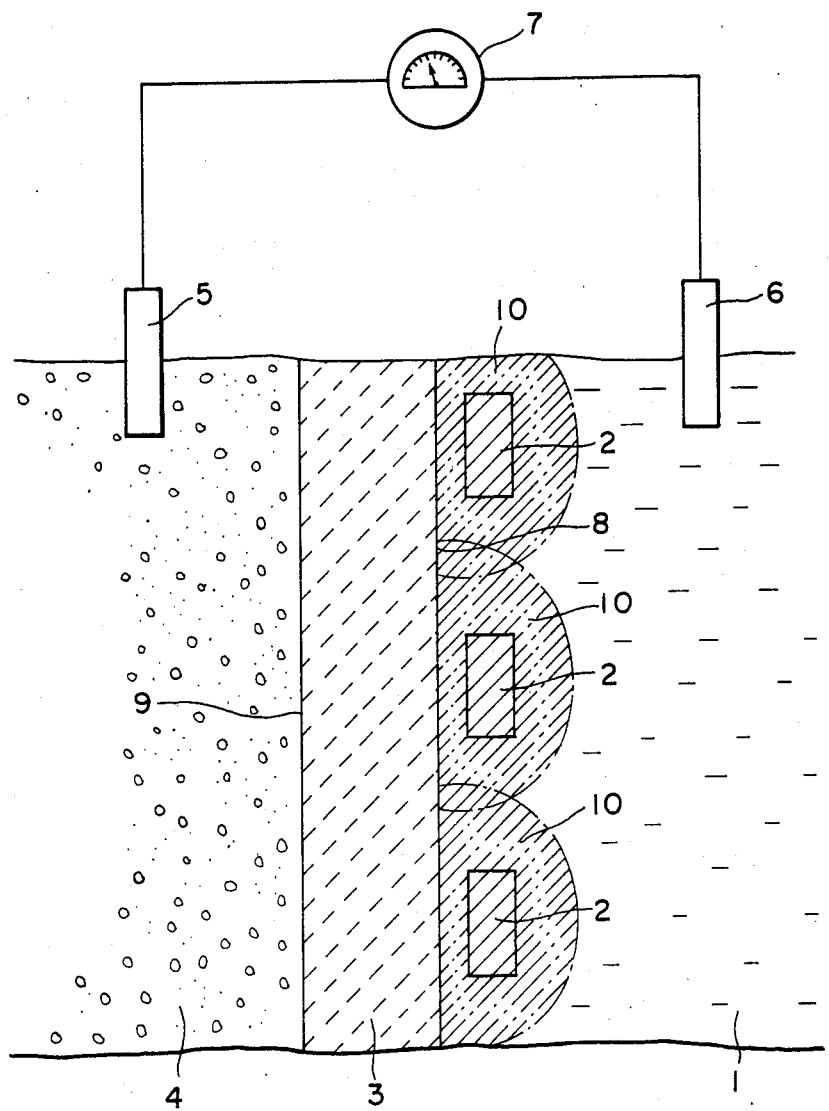
FIG. 2 is a similar view for illustrating a principle underlying the determination of the silicon concentration in accordance with the invention, in which the auxiliary electrode is disposed at a location slightly spaced apart from a surface of the solid electrolyte layer.

FIGS. 1 and 2 are conceptual views for illustrating a principle underlying the determination of the silicon concentration in accordance with the invention. In these figures, the reference numeral 1 designates a molten metal, the reference numeral 2 an auxiliary electrode, the reference numeral 3 a layer of a solid electrolyte capable of conducting oxygen ions, the reference numeral 4 a reference electrode, the reference numeral 5 a lead line of the reference electrode side, the reference numeral 6 a lead line of the molten metal side, and the reference numeral 7 a potentiometer. The means for determining a potential difference between the reference electrode and the molten metal referred to herein comprises the lead lines 5 and 6, and the potentiometer 7. The reference numeral 8 designates that surface of the solid electrolyte layer 3 which is to be brought in contact with the molten metal 1 and which will be referred to briefly as an outer surface of the solid electrolyte layer 3, while the reference numeral 9 designates that surface of the solid electrolyte layer 3 which is in contact with the reference electrode 4 and which will be referred to briefly as an inner surface of the solid electrolyte layer 3.

The molten metal 1 may be a molten pig iron, a molten steel or a molten non-ferrous metal. The invention will be illustrated regarding the case wherein the molten metal is a molten pig iron. The auxiliary electrode 2 comprises $SiO_2$. It may consist of $SiO_2$. Preferably it consists of a refractory oxide containing $SiO_2$. A preferred refractory oxide is a two phase mixture of $ZrO_2$ and $ZrSiO_4$, which may be prepared by calcining a mixture of particulate $ZrSiO_4$ and a paste of $ZrO_2$ for example, at a temperature of about 1300° to about 1500° C. A preferred material for the solid electrolyte 3 for conducting oxygen ions is at least partly stabilized $ZrO_2$ which is known in connection with the conventional oxygen sensors. As the stabilizer use can be made of MgO and CaO, as is the case with the conventional oxygen sensors. A preferred solid electrolyte consists essentially of $ZrO_2$ stabilized with about 7 to 9% by mole of MgO. The reference electrode for providing a constant oxygen potential at a particular temperature of measurement may consist of a mixture of particulate Mo and particulate $MoO_2$, or a mixture of particulate Cr and particulate $Cr_2O_3$, as is the case with the conventional oxygen sensors. The materials constituting the solid electrolyte 3 and the reference electrode 4 may be those known in connection with the conventional oxygen sensors, and do not constitute novel features of the invention.

FIG. 1 shows the case wherein the auxiliary electrode 2 is supportedly secured on the outer surface 8 of the solid electrolyte layer 3, while FIG. 2 shows a case wherein the auxiliary electrode 2 is disposed at a location slightly spaced apart from the outer surface 8 of the solid electrolyte layer 3. In any event the outer surface 8 of the solid electrolyte layer 3 msut be existent in the chemical quasi-equilibrium zone formed by the auxiliary electrode 2 immersed in the molten pig iron. The chemical quasi-equilibrium zone 10 is conceptually shown in FIGS. 1 and 2 by areas hatched with dotted lines.

The potentiometer 7 is to detect a difference in oxygen potentials between the chemical quasi-equilibrium zone 10 and the reference electrode 4. While the oxygen potential in the chemical quasi-equilibrium zone 10 may differ from that in the bulk of the molten pig iron 1, the activity of silicon in the chemical quasi-equilibrium zone 10 does not normally differ from that in the bulk of the molten pig iron 1 to a great extent. Since these conditions are practically met by a normal molten pig iron, as discussed herein-above, the potential difference detected by the potentiometer 7 substantially reflects the silicon content of the molten pig iron 1. This general relationship between the activity of silicon and the oxygen potential in the chemical quasi-equilibrium zone 10 and that in the molten metal 1 are shown in FIG. 3.

Figure 3:
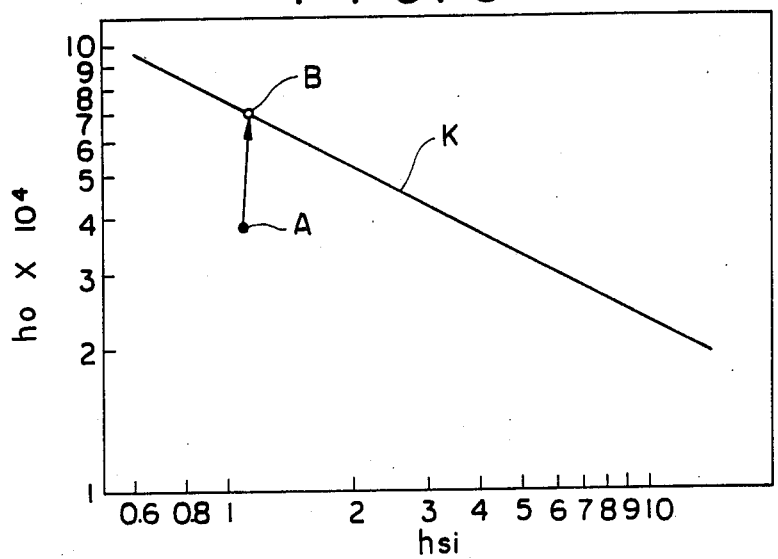
FIG. 3 is a graphic depiction of the relationship between the activity of silicon and the oxygen potential in the chemical quasi-equilibrium zone formed in accordance with the invention, and that in the molten metal.

In FIG. 3, the straight line K shows an equilibrium relation between the thermodynamic oxygen and silicon potentials in the chemical quasi-equilibrium zone. The axes of ordinates and abscissas represent the activities of oxygen and silicon, respectively, both on Henry basis and on a logarithmic scale. It should be noted, however, that while the axis of abscissas represents the activity of silicon $h_{si}$ in itself, the axis of ordinates represents the activity of oxygen $h_o$ multiplied by $10^4$. Suppose that a case wherein Point A represents the oxygen and silicon potentials in the molten pig iron and Point B represents those in the chemical quasi-equilibrium zone. While the oxygen potentials represented by Points A and B display a considerable numerical difference, the silicon potentials represented by Points A and B do not display a significant difference. In order that this condition is met, the oxygen content of the molten pig iron should be about 150 ppm by weight or less, preferably about 100 ppm by weight or less, and the silicon content of the molten pig iron should preferably be at least about 0.1% by weight. Generally, the greater the difference between the oxygen and silicon contents in the molten metal, the more likely this condition is met. In cases wherein the difference between the oxygen and silicon contents in the molten metal is small, the detected potential difference does not necessarily directly correspond to the silicon content of the molten metal. However, this difficulty may be overcome by suitably correcting the detected value based on experimentally predetermened calibration curves. Thus, it is possible to determine the silicon content of a molten pig iron by the method according to the invention, even if it is as low as about 0.01%.

Advantageous arrangements of the auxiliary electrode 2 and the solid electrolyte layer 3, which ensure that the outer surface 8 of the solid electrolyte layer 3 may be placed in the chemical quasi-equilibrium zone formed by the auxiliary electrode 2, will now be described with reference to FIGS. 4 to 14.

Figures 4, 5, 6:
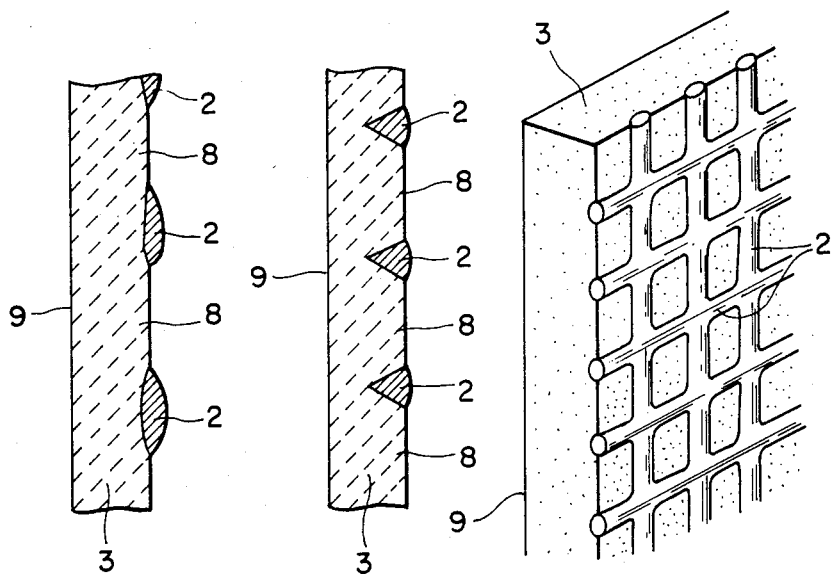
FIG. 4 is a schematic cross-sectional view showing an arrangement of the solid electrolyte layer and the auxiliary electrode in accordance with the invention.
FIG. 5 is a schematic cross-sectional view showing another arrangement of the solid electrolyte layer and the auxiliary electrode in accordance with the invention.
FIG. 6 is a schematic cross-sectional view showing a further arrangement of the solid electrolyte layer and the auxiliary electrode in accordance with the invention.

According to the embodiment shown in FIG. 4, the outer surface 8 of the solid electrolyte layer 3 is partly coated with a plurality of discrete spots of the auxiliary electrode 2, each of a small surface area.

In the embodiment shown in FIG. 5, the outer surface 8 of the solid electrolyte layer 3 is provided with many small incisions or cavities, where the spots of the auxiliary electrode are buried so that the outer surfaces of the auxiliary electrode may be exposed.

Alternatively, the auxiliary electrode 2 may be secured on the outer surface 8 of the solid electrolyte layer 3, for example, in a lattice layout as shown in FIG. 6.

Figure 7:
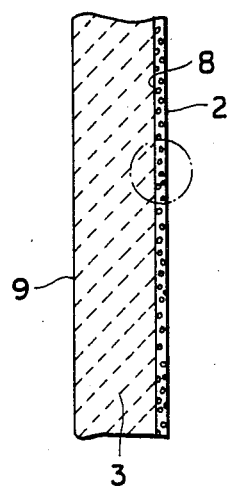
FIG. 7 is a schematic cross-sectional view showing a still further arrangement of the solid electrolyte layer and the auxiliary electrode in accordance with the invention.
Figure 8:
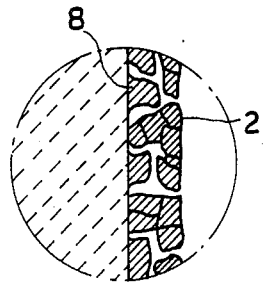
FIG. 8 is an enlarged view of a part of the auxiliary electrode shown in FIG. 7.

FIG. 7 depicts an example, in which the outer surface 8 of the solid electrolyte layer 3 is coated with a porous material constituting the auxiliary electrode. A part of the coated layer is enlarged and shown in FIG. 8. As seen from FIG. 8, in the layer of the auxiliary electrode 2 there are many intergranular channels, through which the outer surface 8 of the solid electrolyte layer 3 communicates with the exterior.

Figure 9:
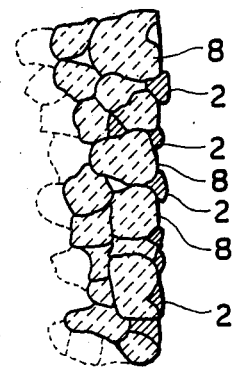
FIG. 9 is a schematic cross-sectional view showing still another arrangement of the solid electrolyte layer and the auxiliary electrode in accordance with the invention.

According to the embodiment shown in FIG. 9, crystalline granules of a material constituting the auxiliary electrode 2 are secured in position between or in the crystalline granules of a material constituting the outer surface 8 of the solid electrolyte layer 3. Such an arrangement may be conveniently prepared by mechanically rubbing a particulate material for forming the auxiliary electrode ( for example, a mixture of particulate $ZrSiO_4$ and a paste of $ZrO_2$ ) onto the outer surface 8 of the solid electrolyte layer 3, and calcining the whole.

Figure 10:
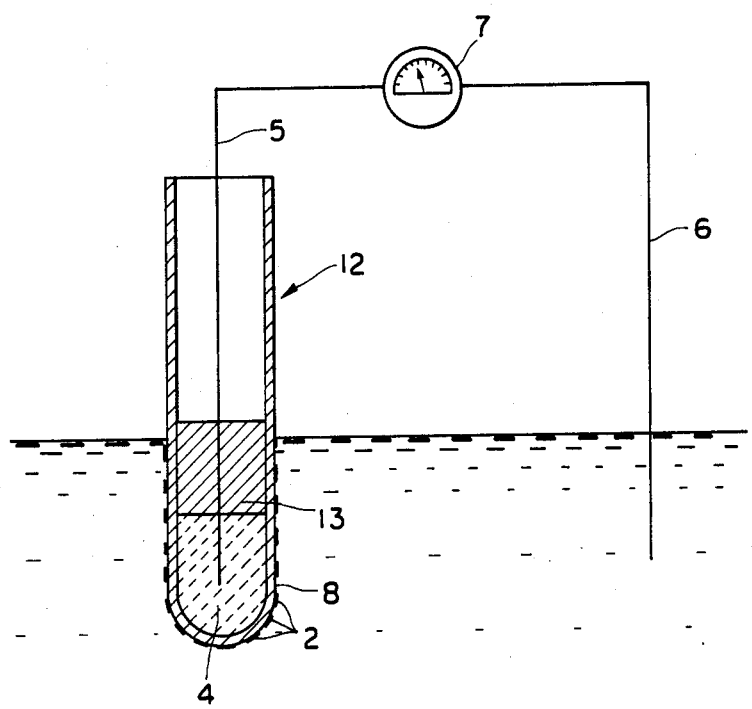
FIG. 10 is a schematic cross-sectional view of an apparatus according to the invention, in which the solid electrolyte layer is in the shape of a tube with one end closed.

FIG. 10 is a schematic cross-sectional view of an apparatus according to the invention, in which the solid electrolyte layer is in the shape of a tube with one end closed. According to a preferred embodiment of the invention, the solid electrolyte layer 3 is in the shape of a tube 12 with one end closed, as shown in FIG. 10. The tube 12 made of the solid electrolyte is filled at the bottom with a material constituting the reference electrode 4, which is sealed by a sealing material 13. The auxiliary electrode 2 is disposed in the manner as illustrated in FIGS. 4–9 on the outer surface 8 of at least that part of the tube 12 where the reference electrode 4 is charged.

Figure 11:
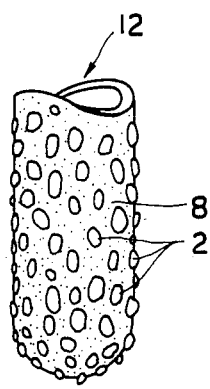
FIG. 11 is a perspective view of a tube-shaped solid electrolyte having an auxiliary electrode in spots on its outer surface.
Figure 12:
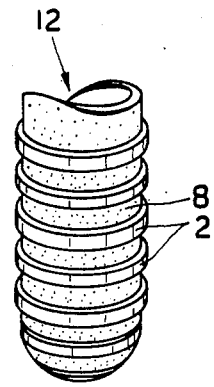
FIG. 12 is a similar view of a tube-shaped solid electrolyte having an auxiliary electrode in transverse stripes on its outer surface.
Figure 13:
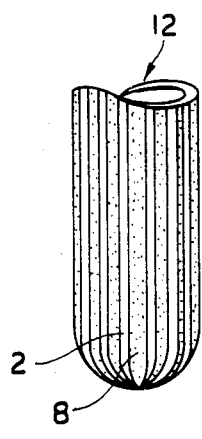
FIG. 13 is a similar view of a tube-shaped solid electrolyte having an auxiliary electrode in longitudinal stripes on its outer surface.
Figure 14:
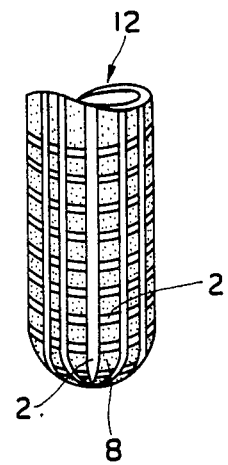
FIG. 14 is a similar view of a tube-shaped solid electrolyte having an auxiliary electrode in a lattice layout on its outer surface.

FIG. 11 is a perspective view of a tube-shaped solid electrolyte 12 having the outer surface 8 coated with an auxiliary electrode 2 in spots. FIG. 12 is a similar view of a tube-shaped solid electrolyte 12 having the outer surface 8 coated with an auxiliary electrode 2 in transverse stripes. FIG. 13 is a similar view of a tube-shaped solid electrolyte 12 having the outer surface 8 coated with an auxiliary electrode 2 in longitudinal stripes. FIG. 14 is a similar view of a tube-shaped solid electrolyte 12 having the outer surface 8 coated with an auxiliary electrode 2 in a lattice layout. The auxiliary electrode 2 as a whole should be distributed on the effective outer surface of the tube 12 as uniformly as possible. We have found that about from 25 to about 95%, preferably from about 30 to about 90%, of the area of the effective outer surface of the tube 12 should preferably be coated with the auxiliary electrode 2. By the term "effective" we mean the outer surface of that part of the tube 12 which acts as an electrolyte for conducting oxygen ions in the actual measurement.

In the embodiments illustrated in FIGS. 4 to 14, the auxiliary electrode 2 is supported on the outer surface 8 of the solid electrolyte layer 3, and thus, the outer surface 8 of the solid electrolyte layer 3 is in contact with the auxiliary electrodes 2. FIGS. 15 to 19 illustrate embodiments according to the invention in which the outer surface 8 of the solid electrolyte layer 3 is not in contact with the auxiliary electrode 2. It is essential, however, that even with the latter embodements all the effective outer surface 8 of the solid electrolyte layer 3 will be present within the chemical quasi-equilibrium zone 10 which will be formed by the auxiliary electrode 2.

Figure 15:
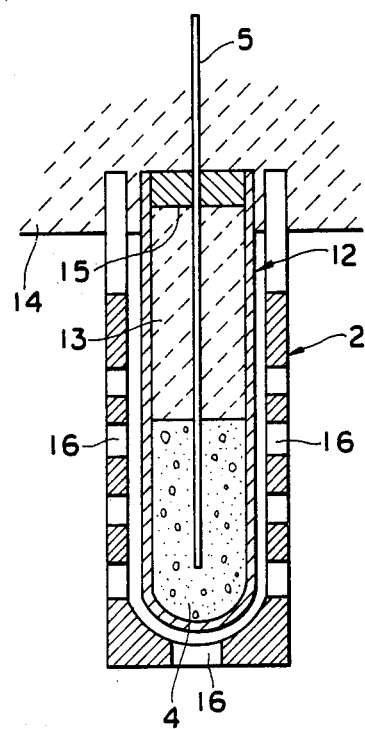
FIG. 15 is a schematic cross-sectional view of a silicon sensor according to the invention in which the auxiliary electrode is disposed at a location slightly spaced apart from the outer surface of the tube-shaped solid electrolyte.
Figure 16A:
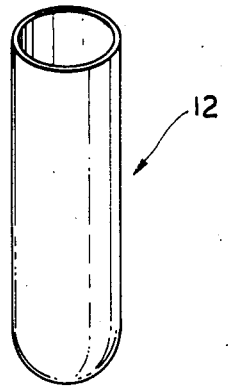
FIG. 16(a) is a perspective view of the tube-shaped solid electrolyte of FIG. 15.
Figure 16B:
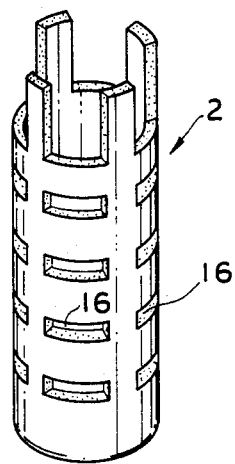
FIG. 16(b) is a perspective view of the auxiliary electrode of FIG. 15.
Figure 16C:
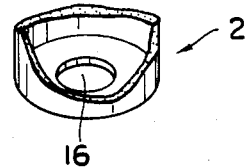
FIG. 16(c) is a partly cut-away perspective view for showing the bottom part of the auxiliary electrode of FIG. 16(b)

FIG. 15 illustrates a silicon sensor according to the invention comprising a tube-shaped solid electrolyte 12 and a tube-shaped auxiliary electrode 2 having an inner diameter slightly larger than the outer diameter of the tube-shaped solid electrolyte 12 disposed so that the tubular electrolyte 12 may be surrounded by the tubular auxiliary electrode 2. Open ends of both the tubular electrolyte 12 and tubular auxiliary electrode 2 are buried in a refractory material 14 so that the desired relative position of them may be secured. In the tubular solid electrolyte 12 a material for constituting the reference electrode 4 is filled and sealed by a sealing material 13 similarly to the case of FIG. 10. To complete the sealing the open end of the tube 12 may be further sealed by a cement layer 15. The reference numerical 5 designates a lead line for the reference electrode 4. The tubular auxiliary electrode 2 is provided with perforations 16 on its side and bottom, through which the molten metal can flow in to reach the outer surface 8 of the tubular solid electrolyte 12. The tubular electrolyte 12 and tubular auxiliary electrode 2 are shown in more detail in FIGS. 16 (a), (b) and (c). FIG. 16(a) is a perspective view of the tubular solid electrolyte 12, FIG. 16(b) is a perspective view of the tubular auxiliary electrode 2 having a plurality of perforations 16, and FIG. 16(c) shows the bottom part of the auxiliary electrode 2 having a perforation 16.

Figure 17:
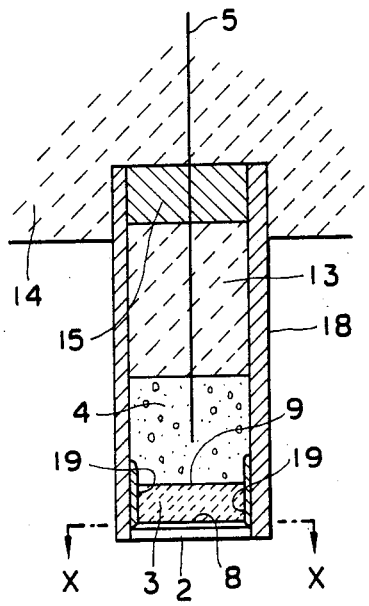
FIG. 17 is a schematic cross-sectional view of another silicon sensor according to the invention.
Figure 18:
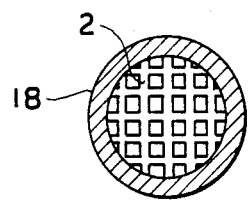
FIG. 18 is a cross-section of the silicon sensor of FIG. 17 taken along the line X—X.

FIG. 17 is a schematic cross-sectional view of another silicon sensor according to the invention, in which the solid electrolyte layer 3 is supported by a tubular supporting member. In the illustrated example, a tube 18 of a refractory material with both ends open is blocked at one end by a disc-shaped layer of the solid electrolyte 3, thereby the solid electrolyte layer 3 is securely supported by the tube 18 at that end, preferably at a location slightly inner from that end. The reference numeral 19 designates a sealing cement for bonding the refractory material of the tube 18 with the solid electrolyte. The tube 18 having the bottom so formed by the solid electrolyte layer 3 is then filled with a material constituting the reference electrode 4 so that the reference electrode may come in contact with the inner surface 9 of the solid electrolyte layer 3. In the manner described with reference to FIG. 15, the reference electrode 4 is sealed in the tube 18 by a sealing material 13 and cement 15, and the assembly so formed is supported by a refractory material 14. The reference numeral 5 designates a lead line for the reference electrode 4. An auxiliary electrode 2 in the shape of perforated plate or lattice is disposed outside of the outer surface 8 of the solid electrolyte layer 3. The edge of the tube 18 extending beyond the outer surface 8 of the solid electrolyte layer 3 serves to support the auxiliary electrode 2. FIG. 18 is a cross-section of the silicon sensor of FIG. 17 taken along the line X—X, showing the lattice-shaped auxiliary electrode 2. The tube 18 and the auxiliary electrode 2 may be made of the same material, and in such a case they can be constructed unitary. In the illustrated example, the auxiliary electrode 2 is disposed slightly spaced apart from the outer surface 8 of the solid electrolyte layer 3. But they may be in contact relation.

Figure 21:
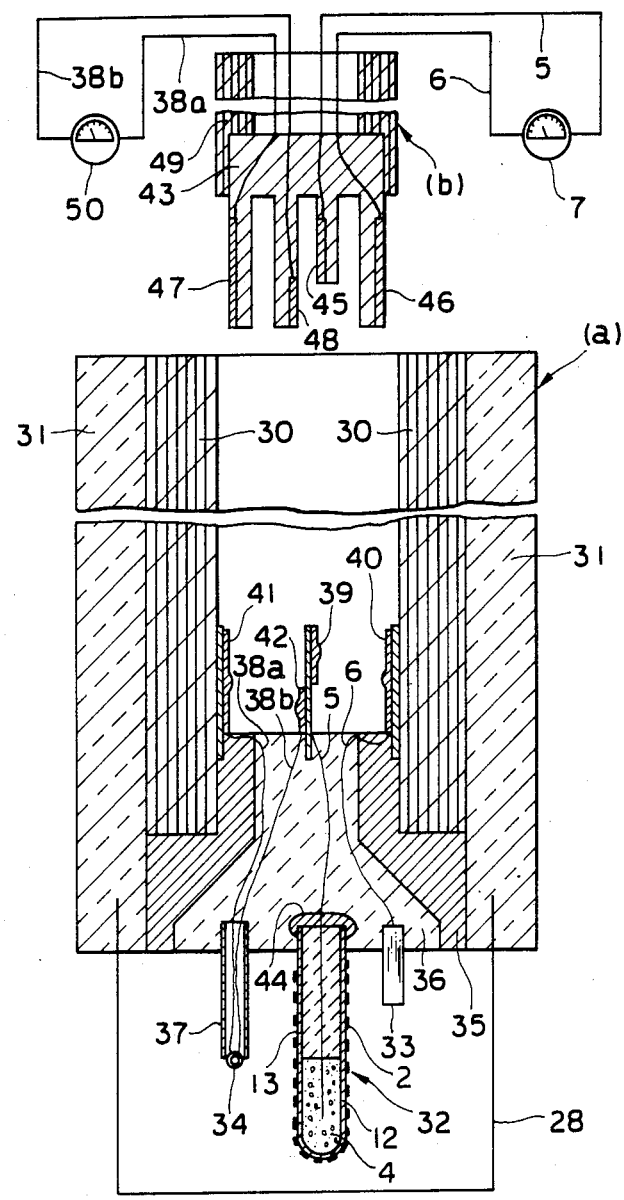
FIG. 21 is an enlarged cross-sectional view of the element of FIGS, 19 and 20.

A preferred apparatus according to the invention will now be described with reference to FIGS. 19 to 21, in which:

FIG. 19 is a persective view of a preferred measuring element in which a silicon sensor according to the invention is incorporated;

FIG. 20 depicts a schematic vertical cross-section of the element of FIG. 19 during measurement together with an arrangement of measuring instruments in a block diagram; and FIG. 21 is an enlarged cross-sectional view of the element of FIGS. 19 and 20.

The illustrated measuring element 22 is convenient for use in the electro-chemical determination of the silicon content of a molten pig iron or steel under refining, normally having a slag layer. As shown in FIG. 19, the element 22 is generally of an elongated cylindrical appearance, and comprises a socket part (a) and a plug part (b) which are in socket and plug relation. The element 22 has sensing members 23, including the silicon sensor according to the invention, which extend longitudinally of the cylindrical element 22 beyond one end thereof. From the opposite end of the element 22, two pairs of conducting wires 24 and 25 are taken out, respectively connected to a potentiometer and a thermoelectric thermometer.

Upon measurement the element 22 is immersed in a molten metal 1 to such an extent that the surface 26 of the molten metal may come about halfway of the length of the element, as shown in FIG. 20. In a case wherein the molten metal 1 is covered by a slag layer 27, the sensing members 23 are frequently contaminated by the slag upon insertion of the element 22 through the slag layer 27 into the molten metal 1. To avoid this, the sensing members 23 are capped with a thin cap 28 made of the same metal as the molten metal. The cap 28 protects the sensing members 23 upon penetration through the slag layer 27, and melts away immediately after the sensing members have come in position for measurement.

The internal structure of the measuring element 22 is shown in FIG. 21. The socket part (a) is provided with sensing members 23, whereas the plug part (b) is removably attached to the socket part (a). The socket part (a) is consumed by one measurement, and thus, can not be used repeatedly, whereas the plug part (b) can be repeatedly used. As shown in FIG. 21, the socket part (a) comprises a tube 30 of coiled paper with the outer surface coated with a layer 31 of a refractory material, the top end open, and the bottom end blocked and equipped with the sensing members 23, including the silicon sensor 32 in accorddance with the invention, a metallic electrode 33 and a thermocouple 34. The socket part (a) may be prepared as follows. A ceramic housing 35 is mounted at one end of the tube 30 of coiled paper, and a cavity in the housing 35 is filled with a refractory cement 36. At this time buried in the refractory cement 36 are top parts of the silicon sensor 32, metallic electrode 33 and tube 37 of the thermocouple 34 as well as the lead lines 5 and 6, and the lead lines 38a and 38b from the thermocouple 34. Socket side connectors 39, 40, 41 and 42, to which the lead lines 5, 6, 38a and 38b are to be connected, respectively, are also secured in position. Finally, the assembly so constructed is coated with the layer 31 of the refractory material. At this time the cap 28 is mounted so as to be supported by the layer 31 of the refractory material. The illustrated silicon sensor 32 may be prepared by filling a tube-shaped solid electrolyte having an auxiliary electrode coated in spots on its outer surface, as shown in FIG. 11, with a material for constituting the reference electrode 4, and sealing the reference electrode 4 by a sealing material 13 ( for example, particulate $Al_2O_3$ ) and an aluminous cement 44. The bottom end of the tube 30 is blocked by the housing 35 and refractory cement 36 so that when the socket part (a) is immersed in the molten metal 1 the molten metal does not enter the inside of the tube 30. In the inside of the tube 30, the socket side connectors 39, 40, 41 and 42 protrude longitudinally upwardly so that they may come in electrical contact with plug side connectors 45, 46, 47 and 48 of the plug part (b), respectively, when the plug part (b) is inserted into the socket part (a). In the illustrated example, the connectors 39 and 45 serve for the lead line 5 from the reference electrode 4 of the silicon sensor 32, the conneccters 40 and 46 for the lead line 6 from the metallic electrode 33, the conneccters 41 and 47 for the lead line 38a from the thermocouple 34, and the conneccters 42 and 49 for the lead line 38b from the thermocouple 34.

The plug part (b) carrying the plug side connectors 45, 46, 47 and 48 comprises a hollow tube 49 of coiled paper having an outer diameter, which is slightly smaller than the inner diameter of the tube 30 of the socket part (a), and a base body 43 mounted at one end of the tube 49 for supporting the plug side connecters 45, 46, 47 and 48. The lead lines 5, 6, 38a and 38b pass through the hollow tube 49, and the lines 5 and 6 are connected to the potentiometer 7, while the lines 38a and 38b are connected to the thermoelectric thermometer 50. In FIGS. 19 and 20, the single reference numeral 24 designates the pair of the lines 5 and 6, while the single reference numeral 25 designates the other pair of the lines 38a and 38b.

An arrangement of instruments for reading the silicon content from electro-motive force signals detected by the silicon sensor in accordance with the invention is shown in FIG. 20 in a block diagram. A/D converters 51 and 52 are connected to the potentiometer 7 and thermometer 50 for converting two series of electric signals (analog) from the silicon sensor to digital signals, which are put in an operator 53 ( micro-computer ), where the input values are operated to values of the silicon content using predetermined conversion formulae. The values are then put out to displayers 54 and 55 for display, and to a printer 56 for printing.

Figure 22:
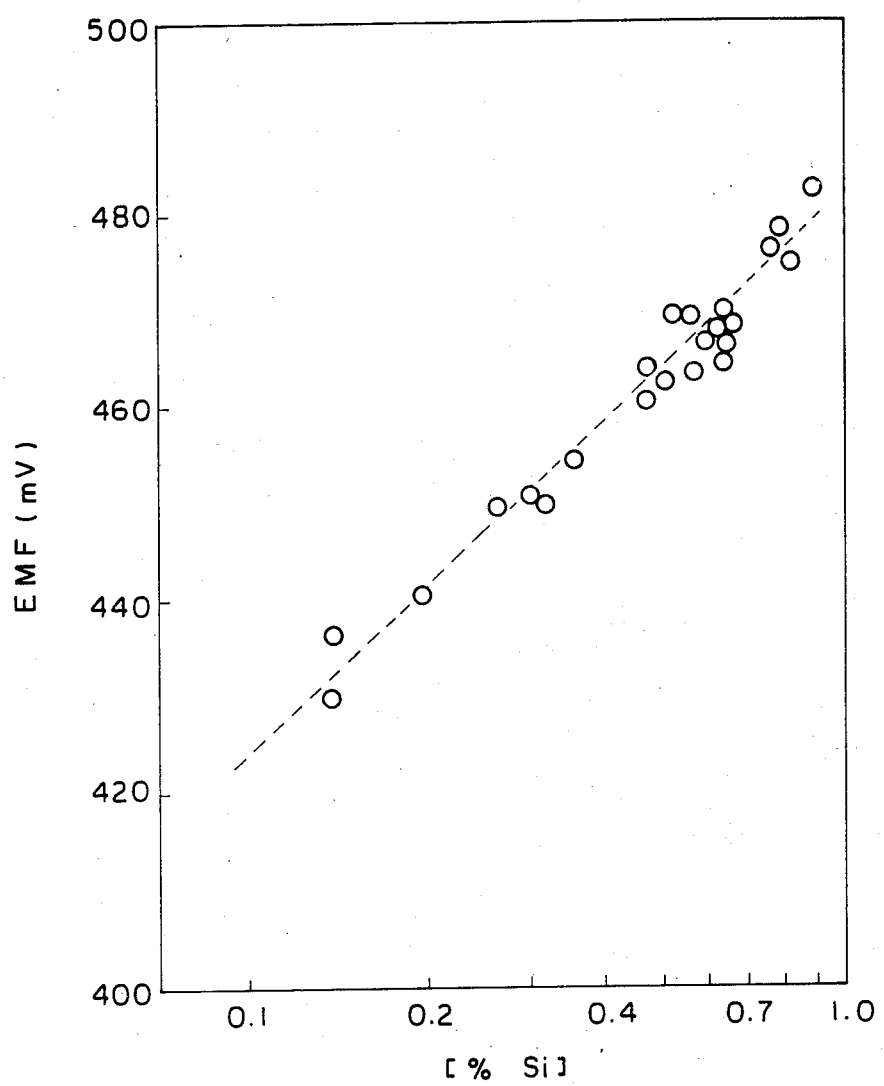
FIG. 22 is a graphic depiction of the relationship between the EMF detected by the method according to the invention and the silicon content.

FIG. 22 shows the EMF detected by means of the silicon sensor according to the invention plotted against the logarithmic silicon content of a molten pig iron. Measurement on which FIG. 22 is based was carried out as follows.

The silicon sensor used in the measurement was of the type as shown in FIG. 21. The used tubular solid electrolyte 12 with one end closed consisted essentially of zirconium dioxide containing as a stabilizer 8.1% by mole of MgO. The material used for forming the auxiliary electrode 2 was a mixture of commercially available first class reagent grade $ZrSiO_4$ passing through a sieve of 200 mesh and a commercially available $ZrO_2$ cement paste. The tubular solid electrolyte 12 was coated with the above-mentioned material in spots as shown in FIG. 11 so that about 50% of the outer surface 8 of the tube 12 was covered by the material. The coated tube was allowed to stand in air for about 2 hours, dried at a temperature of about 100° C. for about one hour and calcined at a temperature of about 1400° C. for about 10 hours. By the calcination the auxiliary electrode 2 in the form of spots firmly adhered to the outer surface 8 of the tube 12.

The tube 12 was filled with a mixture of particulate Mo and particulate $MoO_2$ in a weight ratio of 4:1 to form the reference electrode 4, which was then sealed by using particulate $Al_2O_3$ as a sealing material 13. A Mo wire having a diameter of about 3 mm was inserted through the sealing material 13 into the reference electrode 4 as the lead line 5 for the reference electrode 4, and finally the open end of the tube 12 was sealed with an aluminous cement 44.

The silicon sensor 32 so prepared and a Mo rod as the metallic electrode 33 were immersed for one minute in 700 g of a carbon saturated molten pig iron having a predetermined silicon content placed in an alumina crucible, and the EMF of the concentration cell so constructed (that is the potential difference between the reference electrode 4 and the metallic electrode 33 ) was measured. As the lead line 6 for the metallic electrode 33 a Fe wire was used. The temperature of the molten pig iron was measured using a Pt-13%Rh/Pt thermocouple, and controlled at 1450° C. during the measurement. The measuring procedure was repeated with various silicon concentrations, which were varied within the range between 0.1 and 0.9% by weight using various amounts of high purity metallic silicon added to the molten pig iron.

The results of the measurement are graphically shown in FIG. 22, which reveals that there is a linear relation between the EMF detected in accordance with the invention and the logarithmic silicon content of the molten pig iron, indicating the fact that it is possible to electro-chemically determine the silicon content of a molten pig iron in accordance with the invention.

What is claimed is:

1. A method for the electro-chemical determination of silicon dissolved in a molten metal, comprising the steps of placing a solid auxiliary electrode comprising $SiO_2$ in the molten metal to form a chemical quasi-equilibrium zone wherein the activity of $SiO_2$ is substantially constant, and measuring a potential difference between the molten metal and a reference electrode providing a constant oxygen potential at a particular temperature of measurement separated from each other by a solid eletrolyte capable of conducting oxygen ions.

2. A method for the electro-chemical determination of silicon dissolved in a molten metal, by means of a device comprising a layer of a solid electrolyte capable of conducting oxygen ions, a reference electrode in contact with one surface of said layer of the solid electrolyte for providing a constant oxygen potential at a particular temperature of measurement, and a means for determining a potential difference between said reference electrode and the molten metal, characterized by placing a solid auxiliary electrode having a constant activity of $SiO_2$ in the molten metal, thereby forming a chemical quasi-equilibrium zone in the vicinity of said auxiliary electrode, the product $[a_{si}] \times [P_{o2}]$ wherein $[a_{si}]$ represents an activity of silicon in the molten metal and $[P_{o2}]$ represents a partial pressure of oxygen in the molten metal, being substantially constant within said chemical quasi-equlibrium zone, bringing the other surface of said layer of the solid electrolyte in contact with said chemical quasi-equilibrium zone, and measuring a potential difference between the molten metal and said reference electrode.

3. The method in accordance with claim 2 wherein said solid electrolyte consists essentially of at least partly stabilized $ZrO_2$ and said auxiliary electrode consists essentially of a two phase mixture of $ZrO_2$ and $ZrSiO_4$.

* * * * *